United States Patent
Kucza et al.

(10) Patent No.: US 9,606,027 B2
(45) Date of Patent: Mar. 28, 2017

(54) METHOD OF COLLECTING, PREPARING AND ANALYSING UNDISTURBED SOIL SAMPLES FOR PURPOSES OF DEFINING SOIL HYDRAULIC CONDUCTIVITY AND EQUIPMENT FOR COLLECTING, PREPARING AND ANALYSING UNDISTURBED SOIL SAMPLES FOR PURPOSES OF DEFINING SOIL HYDRAULIC CONDUCTIVITY

(71) Applicant: UNIWERSYTET ROLNICZY IM. HUGONA KOLLATAJA, Cracow (PL)

(72) Inventors: Jaroslaw Kucza, Cracow (PL); Anna Ilek, Ustrzyki Dolne (PL)

(73) Assignee: UNIWERSYTET ROLNICZY IM. H. KOLLATAJA, Cracow (PL)

( * ) Notice: Subject to any disclaimer, the term of this patent is extended or adjusted under 35 U.S.C. 154(b) by 351 days.

(21) Appl. No.: 14/379,293

(22) PCT Filed: Jan. 4, 2013

(86) PCT No.: PCT/PL2013/000001
§ 371 (c)(1),
(2) Date: Aug. 16, 2014

(87) PCT Pub. No.: WO2013/125965
PCT Pub. Date: Aug. 29, 2013

(65) Prior Publication Data
US 2015/0033879 A1    Feb. 5, 2015

(30) Foreign Application Priority Data

Feb. 20, 2012  (PL) .................................... 120781 U
Feb. 20, 2012  (PL) ........................................ 398167
Feb. 20, 2012  (PL) ........................................ 398168

(51) Int. Cl.
G01N 1/08    (2006.01)
G01N 33/24   (2006.01)
G01F 22/00   (2006.01)

(52) U.S. Cl.
CPC ............... *G01N 1/08* (2013.01); *G01F 22/00* (2013.01); *G01N 33/241* (2013.01); *G01N 33/246* (2013.01)

(58) Field of Classification Search
CPC .............................. G01N 1/08; G01N 33/246
See application file for complete search history.

(56) References Cited

U.S. PATENT DOCUMENTS

2010/0089124 A1    4/2010  Katti et al.

FOREIGN PATENT DOCUMENTS

| DE | 19508286 A1 | 2/1996 |
|----|-------------|--------|
| PL | 389934 A1   | 4/2010 |
| PL | 389144 A1   | 4/2011 |

OTHER PUBLICATIONS

Polish Norm PN-55/B-04492, Apr. 25, 1955, drawing.

*Primary Examiner* — Erika J Villaluna
(74) *Attorney, Agent, or Firm* — Andrew Malarz

(57) ABSTRACT

A container consists of two external cylinders: bottom and top, between which a middle cylinder, designed for a sample, is situated. A method of collecting, preparing and analyzing undisturbed soil samples to define soil hydraulic conductivity generally bases on measurement of volume of water flowing through the sample as a function of time and temperature at a defined hydraulic drop. An equipment consists of a base (6) with a perforated socket (7) to which a pressure column (10) is fitted disconnectedly. A lower edge of the column (10) turns into a flange (11) with holes for screws (12) corresponding to openings made in the base (6). In the base (6) there are horizontal deaeration ducts (8)

(Continued)

connected to a vacuum pump. The ducts (8) reach the first grooves of the socket (7). The whole is situated in the external cylinder (17).

16 Claims, 6 Drawing Sheets

METHOD OF COLLECTING, PREPARING AND ANALYSING UNDISTURBED SOIL SAMPLES FOR PURPOSES OF DEFINING SOIL HYDRAULIC CONDUCTIVITY AND EQUIPMENT FOR COLLECTING, PREPARING AND ANALYSING UNDISTURBED SOIL SAMPLES FOR PURPOSES OF DEFINING SOIL HYDRAULIC CONDUCTIVITY

CROSS-REFERENCE TO RELATED APPLICATIONS

This application is the US national stage of the International Application No. PCT/PL2013/000001 and claims pursuant to 35 U.S.C. 119 and the Paris Convention Treaty the benefit of Polish Patent Applications No. P.398167 and No. P.398168 and the Polish Utility Model Application No. W.120781 filed on Feb. 20, 2012, the contents of which are incorporated herein by reference.

BACKGROUND OF THE INVENTION

Field of the Invention

The invention relates to an instrument consisting of a container for collection of undisturbed soil samples, a method of collecting, preparing and analysing undisturbed soil samples, and an equipment for defining soil hydraulic conductivity in laboratory conditions.

Brief Description of the Background of the Invention Including Prior Art

Infiltration properties of soil are a very important question for several areas of science and industry, for instance geology or hydrology. Therefore in laboratory research on water permeability of key significance is collection of material to be analysed, its preparation and performing the analysis in such conditions and using such equipment that will guarantee reliable and repeatable results.

Especially in anisotropic soils, presence of dry particles and root systems directly influences filtration properties of such soil. In case of forest soils, there is another factor determining the value of hydraulic conductivity, namely high content of organic matter in various stages of decay, coming from organic matter falling down and dead roots. These elements have a significant impact on results, as water infiltrating downward goes around such obstacles (soil skeleton and root systems). For the results to be reliable and reflecting reality, the collected soil sample must retain its natural structure, i.e. be physically as similar to natural conditions as possible, otherwise the measurements will be prone to a huge error (reaching up to several hundred percent).

Numerous methods of analysis of hydraulic conductivity, both on-site and in laboratory conditions, have been described in literature, suggesting existence of several methods and devices used for the purpose of such research. In commonly used methods, collecting undisturbed soil samples is only possible in case of uniform soils, i.e. sand, clay/silt, dust. If, however, the sample is to contain the so-called skeleton and root system, the problem starts. It is even more problematic if the soil to be analysed comes from slopes of various gradients and samples should reflect natural water flow (consistent with the direction of gravitational infiltration).

The generally applied method of soil sampling is the removal of soil with a cutting ring. Frequently, a sample obtained in this way is tested without further processing. Sometimes, if the structure of the sample was compromised during sampling, it is homogenised. The prepared sample is placed in a pressure column, and later saturated with water. Then a pressure similar to the one that would be exerted on the sample in natural conditions is produced in the column. The defining of hydraulic conductivity is based on the linear Darcy's Law and means the measurement of the volume of water flowing through the sample and escaping through designated openings in a specified time, with specified hydraulic drop and temperature. In methods known in state of the art, the flow of the water is usually not aligned with the natural direction of filtration which generates further distortions in the results achieved.

Known from the Polish patent application no. P.389144 is a device for simultaneous sampling of monolith and samples of soft deposits. The device is equipped with the upper and lower cones, whose bases are permanently connected with the semi-cylindrical wall of the tube. In turn, the bases are connected with axles, in a semi-turn manner, to the thrust runner, whose one part is set in a semi-cylindrical wall. Mounted to it is a vertical column of the measurement cylinders for deposit samples cut out with the cylindrical blade situated below, while the device is being plunged. At the desired depth, the horizontal rotation of the pole cuts out a semi-cylindrical monolith of the analysed structure with its vertical edge and encloses it together with the samples in the device.

Known from the Polish patent application no. P.389934 is a set for sampling soil profiles. The set consists of a cylinder with an extruder, with arms and connector set on the edges, and a lever which is connected to the mast by means of hinges. Mounted on the mast is a grip, which is fixed in the sockets of the frame in a way enabling disconnection. While pressing the soil profile, the cylinder is placed in the stabiliser.

Known from general use is the ZW-K2 device produced in Poland, which consists from a double steel vessel with water inlets and outlets, a system for lateral deaeration, millimeter scales, perforated base of the internal vessel with mesh size of 0.2 mm, a ring (form) of 113 mm in diameter and 60 mm in height, the top cap with a mesh of 0.2 mm and a weight. This device is equipped with a bottom deaeration system which consists of a number of ducts situated under the sample, which frequently become disconnected while assembling the container with a sample. It is equipped with containers with a flange securing them in the device with the use of screws. Damage of the screws securing the container with the sample results in the destruction of the entire device. The height of the containers is set and amounts to 6 cm, which renders testing of soil strata with thickness below 6 cm impossible. The device allows achieving the maximum hydraulic drop of 2.0, which does not allow testing water permeability of poorly permeable soils.

Soil samples obtained with such devices have strongly compromised structure. The root systems and soil skeleton contained in the sample are shifted. Lack of proper preparation of the sample and also testing it in conditions that are clearly different from the natural conditions result in results fraught with errors difficult even to estimate.

Most of the factors influencing the origination of irregularities in the process of sampling, preparation, and measurements conducted was eliminated thanks to the development of the solutions below.

SUMMARY OF THE INVENTION

Purposes of the Invention

It is an object of the present invention to provide a method of collecting, preparing and analysing undisturbed soil samples for purposes of defining soil hydraulic conductivity and an equipment for collecting, preparing and analysing undisturbed soil samples for purposes of defining soil hydraulic conductivity to avoid irregularities in a process of sampling, preparation, and measurements.

These and other objects and advantages of the present invention will become apparent from the detailed description, which follows.

BRIEF DESCRIPTION OF THE INVENTION

A method according to the invention consists in the gradual formation of a cylinder-shaped sample from the soil profile obtained on site by cutting the extending fragments of the roots and removing the fragments of the skeleton penetrating the surface. While making a profile of the sample, its upper surface is loaded with a metal ring whose diameter is smaller than the diameter of the sampling container and the mass similar to that of the soil overlying the upper level of the sampled soil stratum. Later, a thin elasto-plastic coating is applied favourably on lateral surfaces of the sample. Thus prepared and protected, the sample is placed in the measuring container whose diameter is greater than the diameter of the sample. Subsequently the space between the sides of the sample and the internal surface of the container is filled with watertight agent, and then the soil sample is cut crosswise along the planes defined by the gap between the cylinders, carefully cutting off the fragments of roots encountered on the way, obtaining the sample proper contained in the middle cylinder. Later, the top and bottom surfaces are photographed, and the bottom surface is covered with brass mesh and the perforated cover, and later the border between the edge of the cylinder and the perforated cover is insulated with non-permeable material. The upper surface is covered with brass mesh, on which a steel grate is superimposed, and the sample is loaded with a perforated ring whose mass is similar to that of the mass of the soil overlying the upper level of the soil stratum from which the sample was taken. If soil skeleton is encountered during the cutting off of the external cylinders, it is to be removed, and the hollow originating from it must be filled in with a non-permeable material. Thus prepared, the sample is saturated with water from the bottom by a gradual shifting of the water table; simultaneously, the sample is deaerated. After the separation of the sample, the direction of filtration is changed, and deaeration of the sample continues. Performed finally is the measurement of the volume of the water flowing through the sample, which is removed from the device and collected in a vessel, in a function of time, with set hydraulic drop and temperature. After performing the measurements, the share of soil and root skeletons in the volume of the sample is determined.

Preferably, the gap between the side of the sample and the internal surface of the container is filled with a watertight expanding agent.

Preferably, the hollows left after removal of the elements of the soil skeleton are filled with non-permeable material, e.g. adhesive, paraffin, or gypsum in insulation layer.

Preferably, the duration of sample saturation is adjusted to its internal structure.

The solution of the device according to the invention consists in the base favourably of stainless steel, supplied favourably with supports, in which a socket with perforated bottom is situated, with the diameter of the socket being favourably greater than the bottom cover of the sample. Situated in the walls of the base of the device are radiating horizontal deaeration channels connected to the first grooves of the socket. The deaeration channels are connected through tubing to a vacuum pump in a way allowing disconnection. Situated around the perforated socket is a smooth ring connected favourably in a way allowing disconnection from the base, with thumb screws is the pressure column in the shape of a cylinder, whose lower edge turns into a flange furnished with holes featuring holes for screws corresponding to the openings made in the base. The pressure column is equipped with an external gauge for showing the water level and an external scale showing the hydraulic drop. From the top, the pressure chamber is connected with a feeding duct to a vessel with deaerated distilled water and a dosing device. The whole is situated in the external cylinder made favourably from stainless steel, whose height is approximately equal to $1/4$ of the height of the entire device, and equipped with side openings for measurement of escaping water. The device is also equipped with a perforated cap on the socket of the device base, which makes it possible to test the filtration ratio for homogenous samples taken to containers of various diameters. An additional element of the device's fittings is a three-armed extruder featuring bolts, which correspond to the holders made in the socket of the device base.

The advantage of the solutions presented is the possibility of taking and preparing a soil sample in such a way that its structure remains undisturbed. Significantly, it became possible to take an appropriate sample from grounds situated on slopes of various inclination, and also testing the sample under the developed conditions imitating the natural ones as accurately as possible. Unlike in the known methods, the flow of water through the sample in the process of testing is consistent with the natural direction of filtration, which allows to eliminate major distortions in the results achieved. In the case of unsaturated samples, there is a possibility of analysing hydraulic conductivity at various humidity levels of the original sample. The application of the solutions described makes it possible to attain high repeatability of the measurements. Moreover, the construction of the device allows also to test the coefficient of gravitational drain and to measure the water permeability of successive samples, which is impossible in the case of the testing devices known and generally applied.

BRIEF DESCRIPTION OF THE DRAWINGS

Further details and features of a method of collecting, preparing and analysing undisturbed soil samples for purposes of defining soil hydraulic conductivity and an equipment for collecting, preparing and analysing undisturbed soil samples for purposes of defining soil hydraulic conductivity, its nature and various advantages will become more apparent from the accompanying drawing and the following detailed description of the preferred embodiment shown in a drawing, in which.

DESCRIPTION OF INVENTION AND PREFERRED EMBODIMENT

Figure 1:
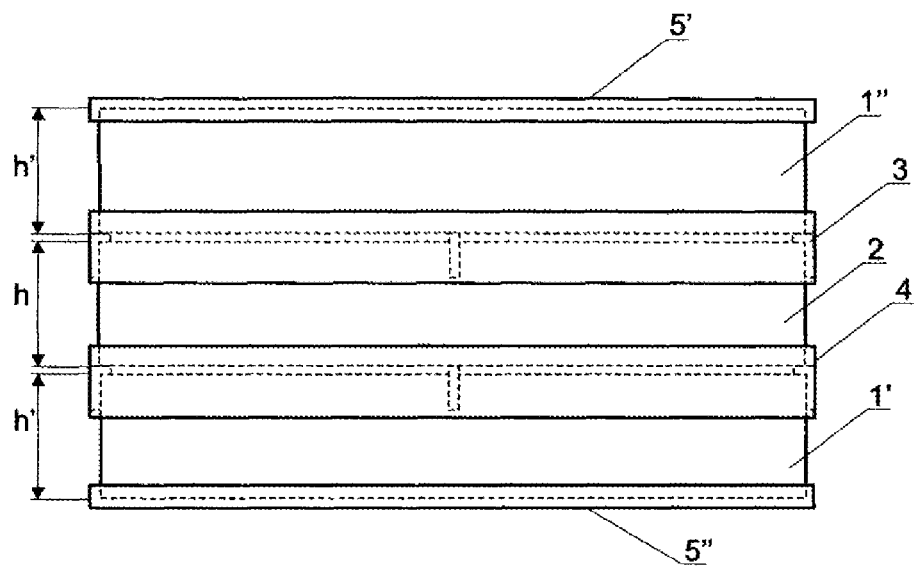
FIG. 1 presents a side view of the container for taking soil samples.
Figure 2:
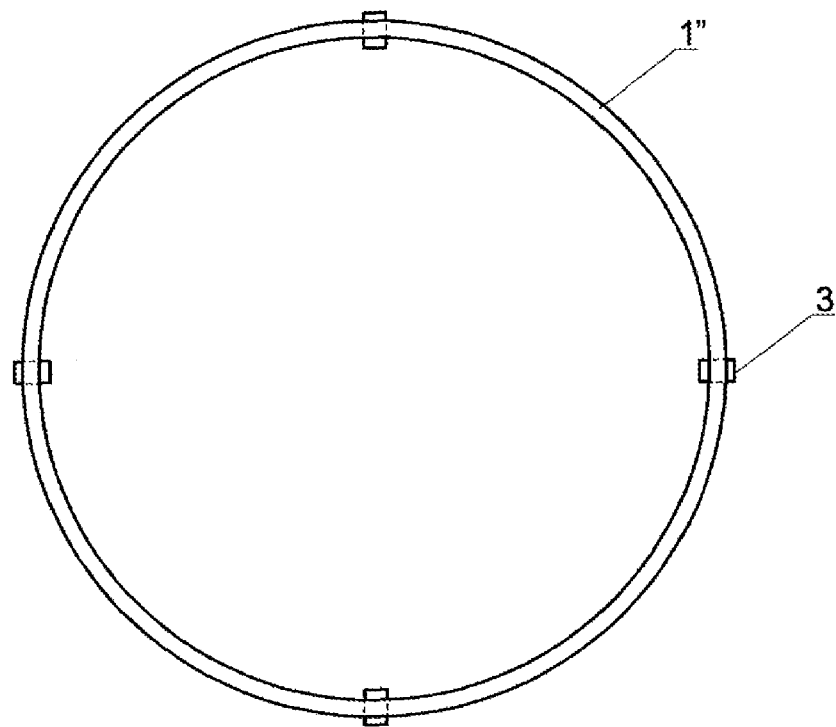
FIG. 2 presents a view of the container without the cover from the top.
Figure 3:
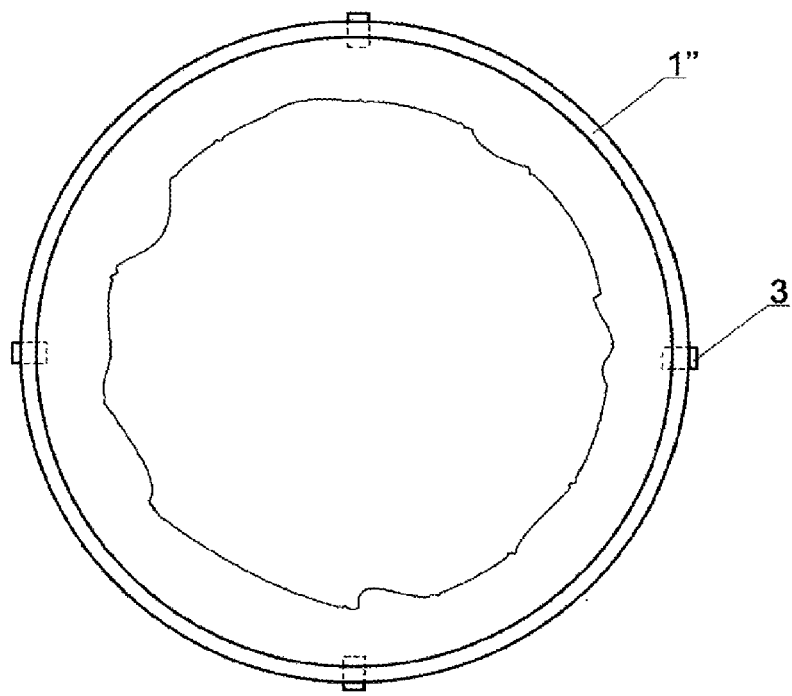
FIG. 3 presents a view of the container from the top with the sample proper inside the middle cylinder.
Figure 4:
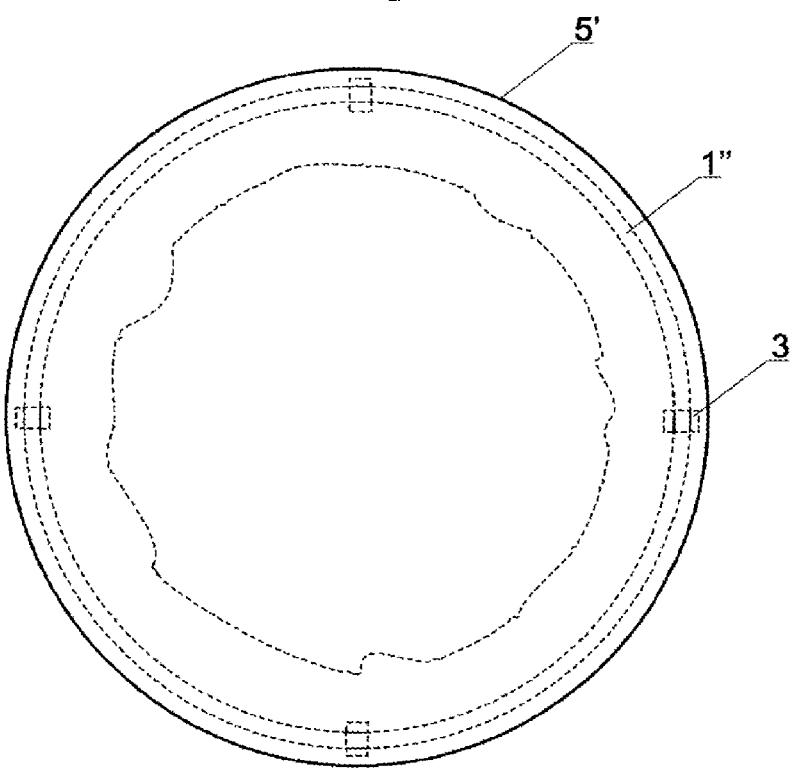
FIG. 4 presents a view of the container from the top with the cover.
Figure 5:
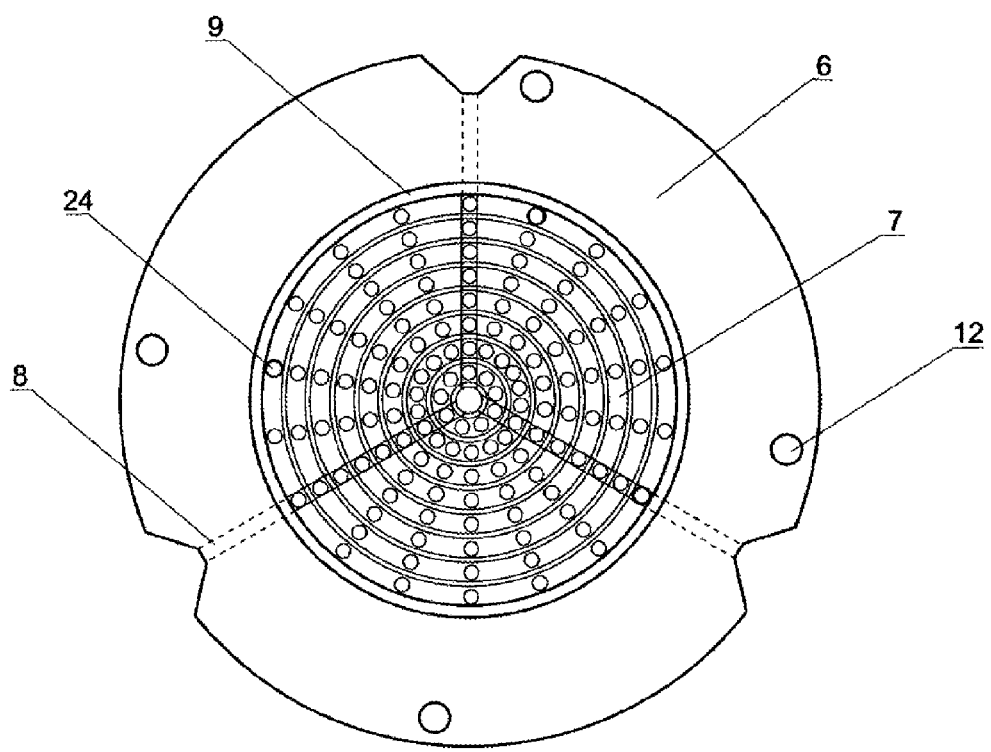
FIG. 5 presents a view from the top of the base of the device for soil filtration analysis.
Figure 6:
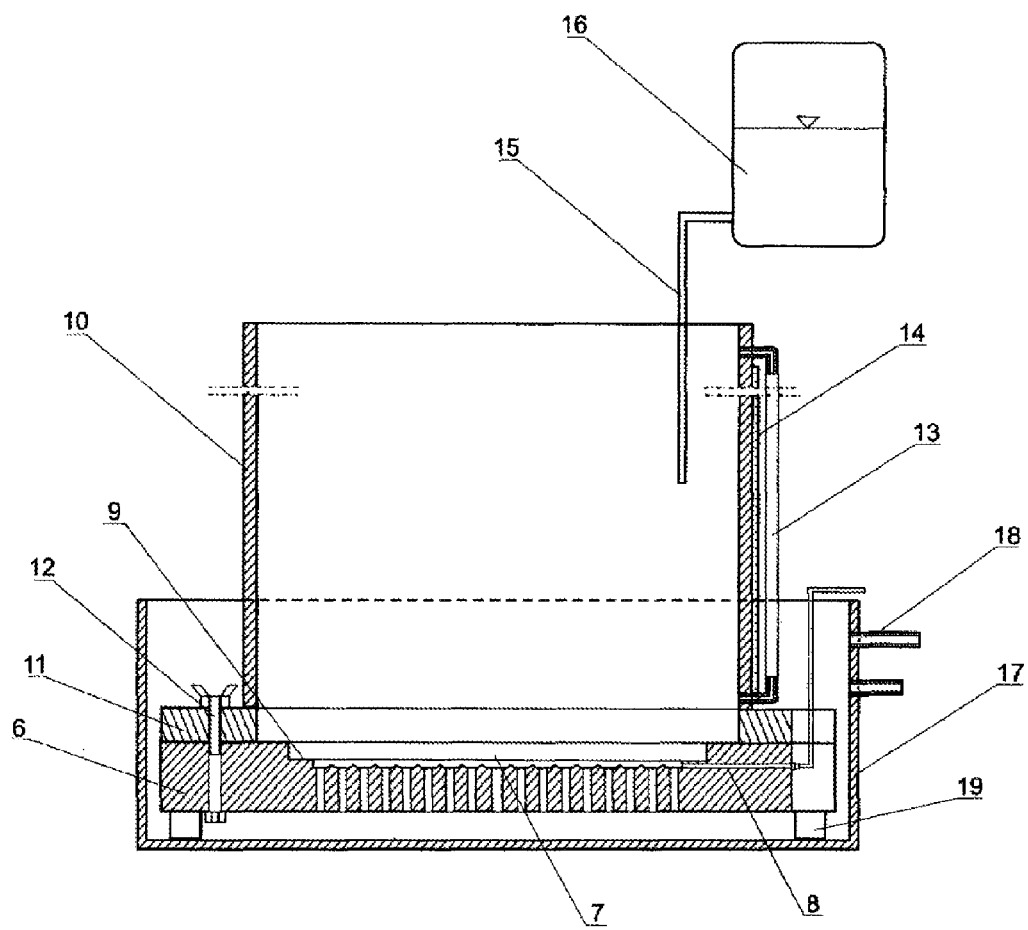
FIG. 6 presents a cross-section of the device in the vertical plane.
Figure 7:
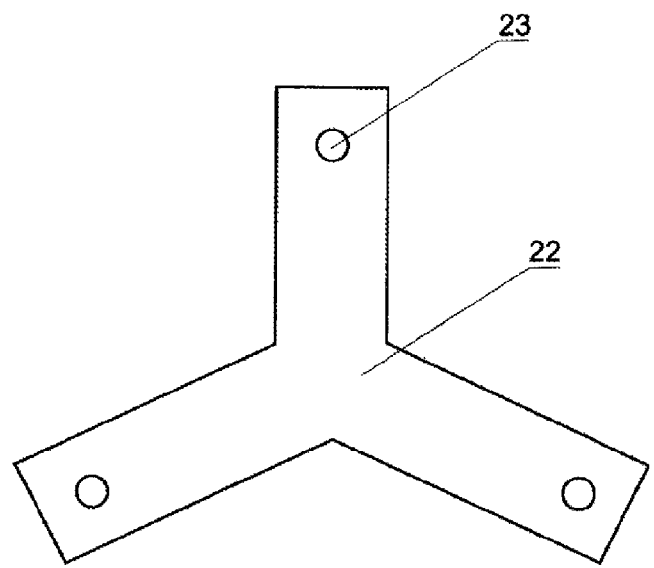
FIG. 7 presents a view from the top of the three-armed extruder.
Figure 8:
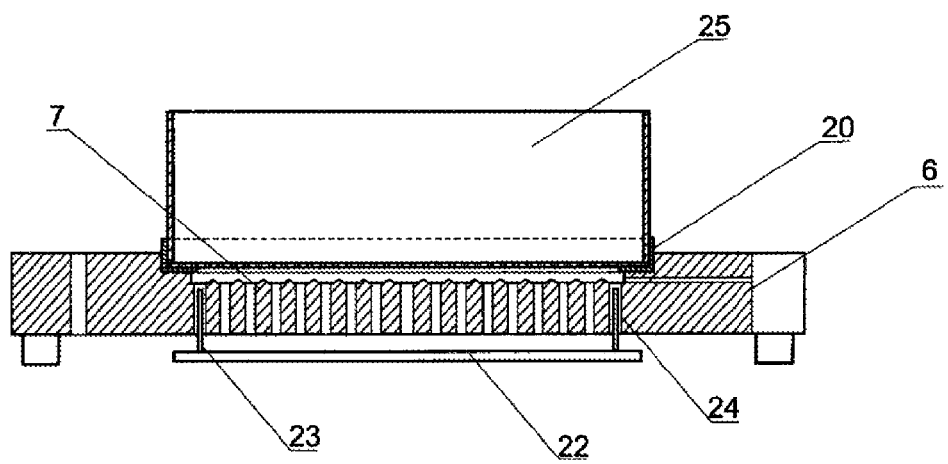
FIG. 8 presents a cross-section of the base with container with the sample mounted in the socket and the three-armed extruder inserted from the side.
Figure 9:
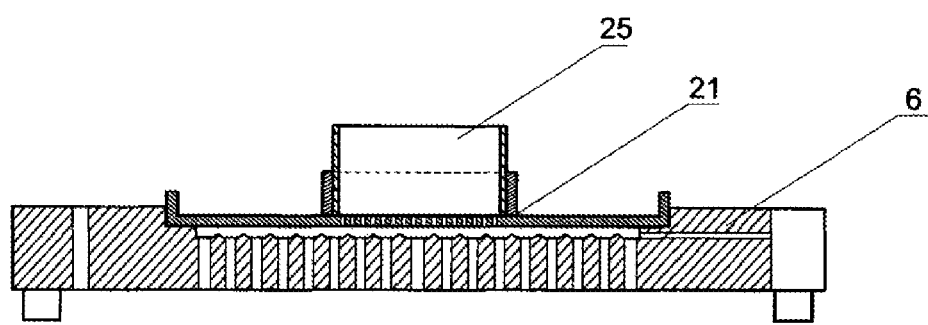
FIG. 9 presents a cross-section of the base with the installed perforated cap.

The embodiments presented in the drawings are intended only for illustrative purpose and do not limit the scope of the invention, as defined by the accompanying claims.

The container for sampling soil consists of two cylinders: bottom 1' and top 1", between which the middle cylinder 2, designed for the sample proper, is situated. The cylinders 1', 1" and 2 are made of stainless steel. Situated between the cylinders 1' and 2, and 2 and 1" are the distancing spacers 3 set at an angle. The cylinders 1', 1" and 2 are connected in our way that allows disconnection and is tight with the non-permeable, self-adhesive tape 4, closely adhering to the external walls of the cylinders. The assembled container is equipped from the top and from the bottom with fitted steel covers 5' and 5". The height h of the middle cylinder 2 is equal to or up to 3 times greater than the height h' of the external cylinders 1' and 1", while the internal diameters of all the cylinders are equal.

Placed in the container is a sample whose diameter is smaller than the diameter of the container, prepared in such a way that the soil profile sampled on site is formed into the initial sample in the shape of a cylinder, from which the protruding fragments of roots are gradually cut off and the fragments of the skeleton penetrating the surface are removed. While profiling a monolith, its upper surface is loaded with a metal disc whose diameter is smaller than the diameter of the container for the sample, whose mass is similar to the mass of soil overlying the upper level of the soil stratum sampled. Then a thin elasto-plastic coating, e.g. of silicon, is applied on the side surface of the sample. After the placement of the sample in the container, the gap between the side surface of the sample and the internal surface of the container is filled with a watertight expanding agent, which can be polyurethane foam, and subsequently the soil sample is cut crosswise along the planes defined by the gaps between this cylinders 1 and 2, and 2 and 1', carefully cutting off the encountered fragments of roots, providing in this way, the sample proper contained in the middle cylinder 2. Now, in turn, the bottom surface of the sample is covered with brass mesh and perforated cover, and subsequently the border between the edge of the cylinder and the perforated cover is insulated with non-permeable material. The upper surface is covered with brass mesh, onto which a steel grate is superimposed and moreover, the sample is loaded with a perforated disc, whose mass is similar to the mass of the soil overlying the upper level of the soil stratum from which the sample was taken. If the soil skeleton is found during the cutting off of the cylinders, it is to be removed delicately, and the hollow thus formed is to be filled with non-permeable matter, e.g. adhesive, paraffin, or gypsum in insulation layer.

Prepared in this way, the sample is placed in the socket 7 of the device for defining hydraulic conductivity. The socket 7 is situated in the round base 6 of the device, made of stainless steel and furnished with supports 19. The socket 7 has a perforated bottom with the diameter of the holes equal to 3.5 mm, with the diameter of the socket being greater than that of the bottom cover 20 of the sample. Situated in the walls of the device base are horizontal deaeration ducts 8 that radiate to the first groove of the socket 7. The deaeration ducts 8 are connected via ducts to a vacuum pump in a way allowing disconnection. Situated around the perforated socket 7 is a smooth ring 9. Connected to the base 6 with thumb screws 12, in a way allowing disconnection, is the pressure column 10 in the shape of a cylinder, whose bottom edge turns into the flange 11, equipped with holes for the screws 12, corresponding to the holes made in the base 6. The pressure column 10 is equipped with an external water level gauge 13 and the external scale 14 indicating the hydraulic drop. From the top, the pressure column 10 is connected via the feeding duct 15 to the vessel 16 with the deaerated distilled water and the dosing device. The whole is situated in the external cylinder 17 made of stainless steel, whose height amounts to approximately ⅓ of the height of the entire device, equipped with side openings 18. The device is also equipped with the perforated reduction sheath 21 for the socket 7 of the device base 6, which allows defining hydraulic conductivity of homogeneous samples sampled into containers of various diameters.

An additional element of the device fittings is a three-armed extruder 22 furnished with bolts, which correspond to the holes 24, made in the socket 7 of the device base 6, used for the removal of the sample from the socket 7 after the completion of analysis.

The sample placed in the device is saturated with water from the bottom by gradual shifting of the water table, at the same time, the sample is deaerated. The duration of sample saturation is adjusted to its internal composition. After saturating the sample, the direction of filtering is changed, and deaeration of the sample continues. Finally, the measurement of the volume of water flowing through the sample is made; the water is removed from the device and collected in a vessel as a function of time at a defined hydraulic drop and temperature.

Due to the presence of the filling agent in the cylinder 2 containing the sample, there is a certain difficulty in calculating the volume and surface of the sample cross-section necessary to define hydraulic conductivity. One of the ways for calculating the surface of the sample, necessary for defining hydraulic conductivity is the determination of its share (in %) in the cross-sectional surface of the cylinder 2. This is why, before the fitting of the sample, both the cross sections of the cylinder (bottom and top) need photographing.

What is claimed is:

1. A method of collecting, preparing and analysing undisturbed soil samples for purposes of defining soil hydraulic conductivity, the method comprising steps
    acquiring on site a lump of soil to be tested;
    forming the lump of soil into an initial sample in a shape of a cylinder;
    cutting off protruding fragments of roots and removing fragments of a skeleton penetrating outer surfaces of the initial sample;
    impositioning a thin elasto-plastic coating on a side surface of the initial sample;
    placing the initial sample in a measurement container with a diameter greater than a diameter of the initial sample and having a bottom cylinder, a top cylinder and a middle cylinder situated between the bottom cylinder and the top cylinder having internal diameters equal to a diameter of the middle cylinder connected to the bottom cylinder and the top cylinder in a way allowing disconnection with a non-permeable tape closely adhering to external walls of the bottom cylinder, the top cylinder and the middle cylinder;

filling with a watertight agent a gap between the side surface of the initial sample and an internal surface of the middle container;

cutting the initial sample along planes defined by gaps between the middle cylinder and the bottom cylinder and the top cylinder to form a soil sample;

cutting encountered fragments of roots protruding beyond the soil sample properly contained in the middle cylinder;

photographing a bottom surface and a top surface of the soil sample;

impositioning a brass mesh and perforated cover on a bottom surface of the soil sample;

insulating a border between an edge of the middle cylinder and the perforated cover with a non-permeable agent;

covering a top surface of the soil sample with a brass mesh and a grid;

placing the soil sample in a socket made in a base placed in an external cylinder and provided with walls, a perforated bottom, a smooth ring situated around the socket and deaerating ducts connected to first grooves of the socket;

attaching the base to a cylinder-shaped pressure column with a bottom edge turning into a flange furnished with holes for screws corresponding to holes made in the base;

loading the soil sample with a perforated disc whose mass is similar to mass of soil overlying a top level of a soil stratum from which the initial sample was taken;

saturating the soil sample from a bottom with water and simultaneously deaerating the soil sample;

changing direction of filtration of the soil sample accompanied by continuing deaeration of the soil sample;

measuring volume of water flowing out from the soil sample with a defined hydraulic drop being made as a function of time and temperature; and determining share of root and skeleton fractions in a volume of the soil sample.

2. The method according to claim 1, wherein the gap between the side surface of the soil sample and an internal surface of the middle container is filled with a watertight expanding agent.

3. The method according to claim 1, wherein hollows after removal of fragments of the skeleton, originating from the cutting off of the soil sample to be proper, are filled up with non-permeable agent, favourably an adhesive, paraffin, or gypsum in an insulation layer.

4. The method according to claim 1, wherein duration of saturating the soil sample is adjusted to its internal construction.

5. An equipment for collecting, preparing and analysing undisturbed soil samples for purposes of defining soil hydraulic conductivity comprising an external cylinder equipped with side openings;

a base placed in the external cylinder and provided with walls, a perforated bottom, a socket and a smooth ring situated around the socket suitable to receive a soil sample and deaerating ducts connected to first grooves of the socket;

a cylinder-shaped pressure column with a bottom edge turning into a flange furnished with holes for screws corresponding to holes made in the base;

an external water level gauge connected to the cylinder-shaped pressure column and an external scale indicating hydraulic drop level;

a container with deaerated distilled water and a dosing device and connected at a top to the cylinder-shaped pressure column; and a measurement container with a diameter greater than a diameter of the initial sample and having a bottom cylinder, a top cylinder and a middle cylinder situated between the bottom cylinder and the top cylinder having internal diameters equal to a diameter of the middle cylinder connected to the bottom cylinder and the top cylinder in a way allowing disconnection with a non-permeable tape closely adhering to external walls of the bottom cylinder, the top cylinder and the middle cylinder surrounding the soil sample when placed in the socket.

6. The equipment according to claim 5, wherein the base is made of stainless steel.

7. The equipment according to claim 5, wherein the base is equipped with supports.

8. The equipment according to claim 5, wherein the diameter of the socket is greater than the diameter of the bottom cover of the sample.

9. The equipment according to claim 5, wherein the pressure column is connected to the base with thumb screws.

10. The equipment according to claim 5, wherein the external cylinder is made of stainless steel.

11. The equipment according to claim 5, wherein situated on the socket of the base is a perforated reducing cap adjusted to containers of various diameters.

12. The equipment according to claim 5, wherein the equipment comprises a three-armed extruder with bolts that correspond to openings made in the socket of the base.

13. The equipment according to claim 5, wherein the measurement container is equipped with a top cover from top and a bottom cover from bottom.

14. The equipment according to claim 5, wherein the bottom cylinder, the top cylinder and the middle cylinder are made of stainless steel.

15. The equipment according to claim 5, wherein the non-permeable tape is a self-adhesive tape.

16. The equipment according to claim 5, wherein the height h of the middle cylinder is equal to a height h' or up to 3 times the height h' of the bottom cylinder and top cylinder.

* * * * *